United States Patent [19]

Doorish

[11] Patent Number: 5,836,996
[45] Date of Patent: Nov. 17, 1998

[54] ARTIFICIAL RETINA

[76] Inventor: John F. Doorish, 1581 E. 12th St., Brooklyn, N.Y. 11230-7101

[21] Appl. No.: 777,075

[22] Filed: Dec. 30, 1996

[51] Int. Cl.$^6$ ..................................................... A61N 1/05
[52] U.S. Cl. ................................ 607/54; 607/116; 623/4; 623/24
[58] Field of Search ............................... 607/53, 54, 116, 607/141; 623/4, 5; 128/898

[56] References Cited

U.S. PATENT DOCUMENTS

| | | | |
|---|---|---|---|
| 4,628,933 | 12/1986 | Michelson | 607/53 |
| 5,024,223 | 6/1991 | Chow | 607/53 |
| 5,109,844 | 5/1992 | de Juan, Jr. et al. | 607/53 |
| 5,397,350 | 3/1995 | Chow et al. | 607/116 X |
| 5,556,423 | 9/1996 | Chow et al. | 607/54 |

OTHER PUBLICATIONS

Dr. Rick Lewis, "Biophotonics in Practice—In Quest of an Artificial Retina," *Biophotonics International*, Jan./Feb. 1997, pp. 36–37.
Stephanie vL Henkel, "Research and Developments—Artificial Retina Component Chip Could Show Shapes and Motion to the Blind," *Sensors*, Feb., 1997, (Internet:http://jollyroger.com/retina).
Cha, et al.,"Research Note, Mobility Performance with a Pixelized Vision System," *Vision Research*, vol. 32, No. 7, pp. 1367–1372, 1992.
Wade Roush, "Envisioning an Artificial Retina," *Science*, vol. 268, pp. 637–638, May 5, 1995.
Dagnelie, et al., "Toward an Artificial Eye," *IEEE Spectrum*, pp. 20–29, May, 1996.
Werblin, et al., "The Computational Eye," *IEEE Spectrum*, pp. 30–37, May, 1996.
Normann, et al., "Cortical Implants for the Blind," *IEEE Spectrum*, pp. 54–59, May, 1996.
Koch, et al., Neuromorphic Vision Chips, *IEEE Spectrum*, pp. 38–46, May, 1996.
Wyatt, et al., "Ocular Implants for the Blind," *IEEE Spectrum*, pp. 47–53, May, 1996.

*Primary Examiner*—Jeffrey R. Jastrzab
*Attorney, Agent, or Firm*—Coudert Brothers

[57] ABSTRACT

The present invention is an artificial retina system that is sufficiently small so as to be fully implantable in the human eye. The artificial retina system comprises an array of artificial retinas. Each artificial retina comprises a light sensing element; an emitter element, where the emitter element is coupled to the light sensing element; and a detector element, where the detector element receives signals from the emitter element. The light sensing element intercepts light and transmits an electrical signal to the emitter element. In response to the electrical signal received from the light sensing element, the emitter element emits a signal. In response to the signal emitted by the emitter element, the detector element transmits an electrical signal to the retinal nerves. The intensity of the electrical signal sent to the retinal nerves is directly proportional to the intensity of the incoming light. In a preferred embodiment, a color filter is placed in front of the light sensing elements such that the light sensing element is limited to receiving light having wavelengths in a wavelength band corresponding to a particular color. In a preferred embodiment, each of the color filters allow passage of a different color of light such that each of the light sensing elements receives light of a different color. Also in a preferred embodiment, the artificial retina includes either a scanning tunneling microscope (STM) tip, a metal sheet, preferably made of copper, or a metal wire disposed between the detector element and the retinal nerves. Each STM tip, metal sheet or metal wire is coupled to a detector element, receives an electrical signal from the detector element and transmits an electrical signal to the retinal nerves.

32 Claims, 10 Drawing Sheets

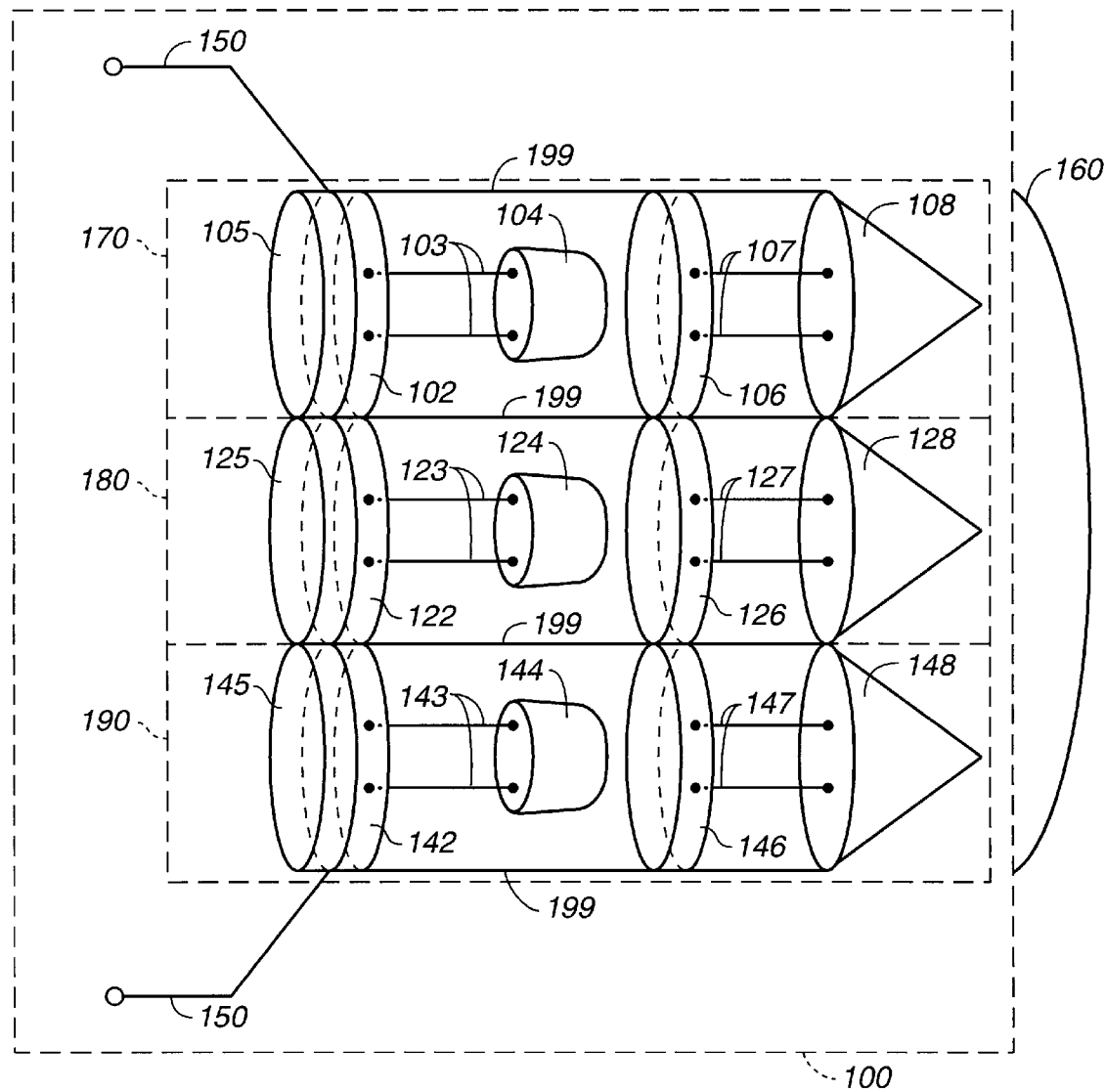
FIG._1A

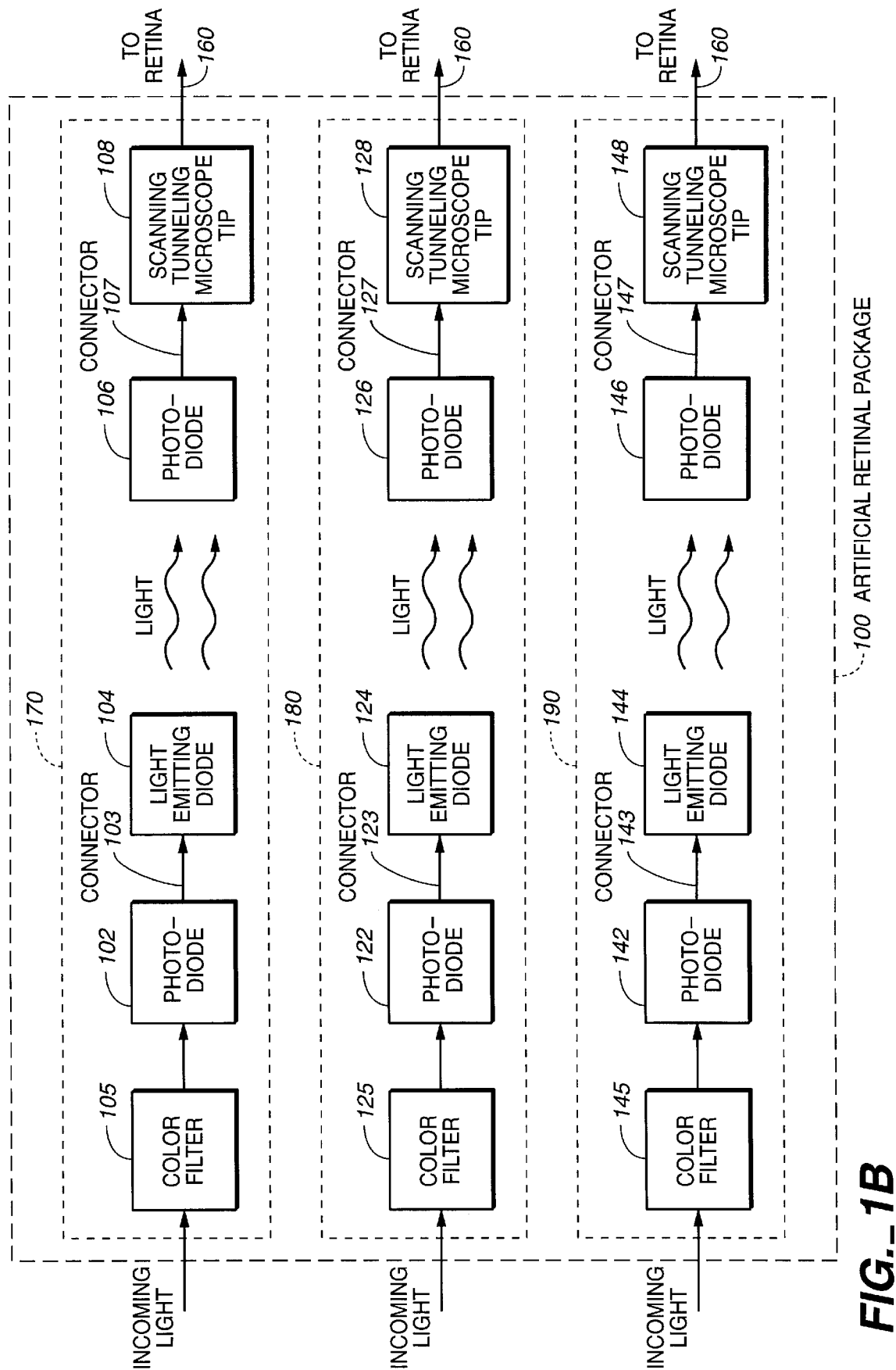
FIG._1B

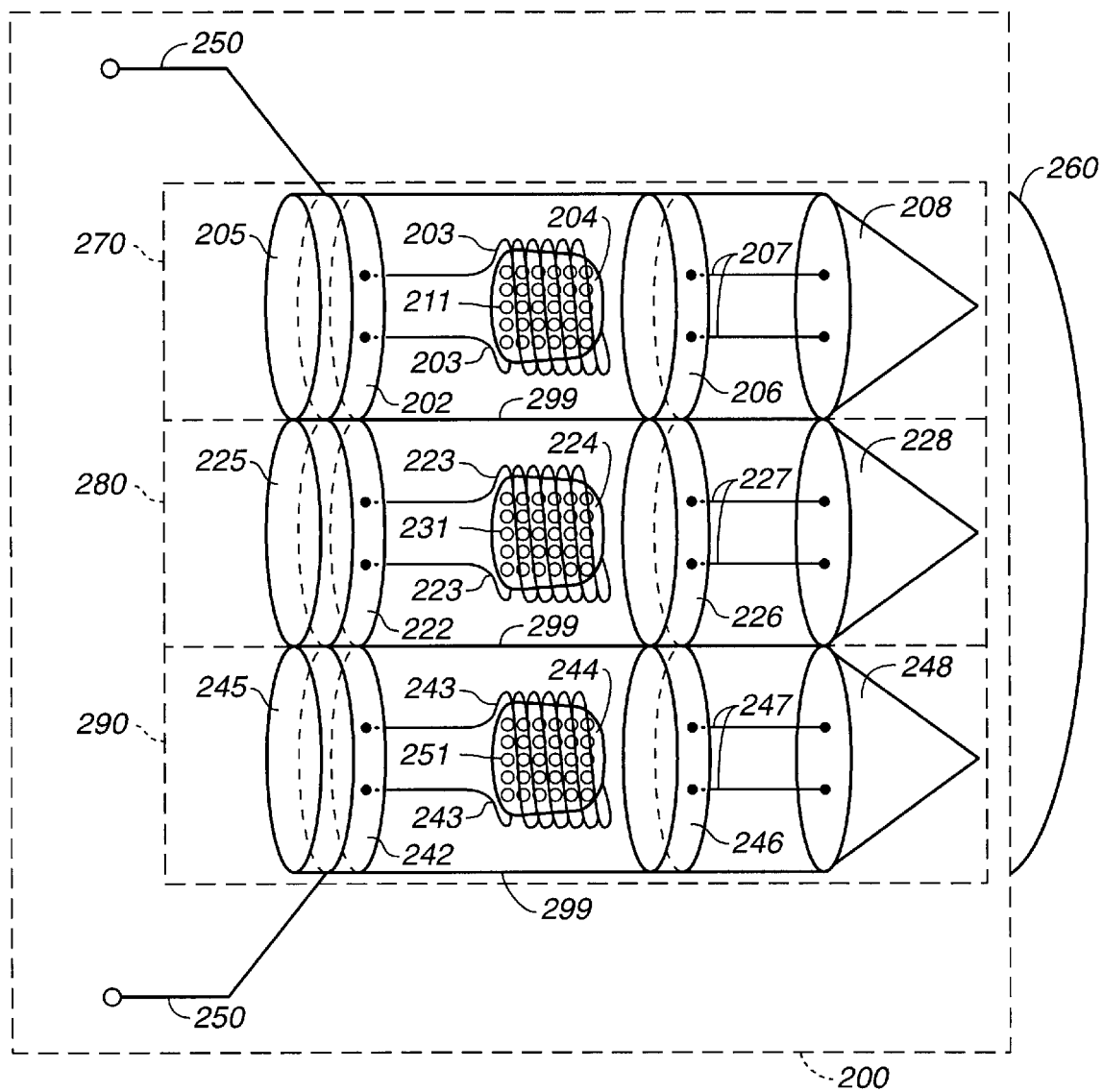
FIG._2A

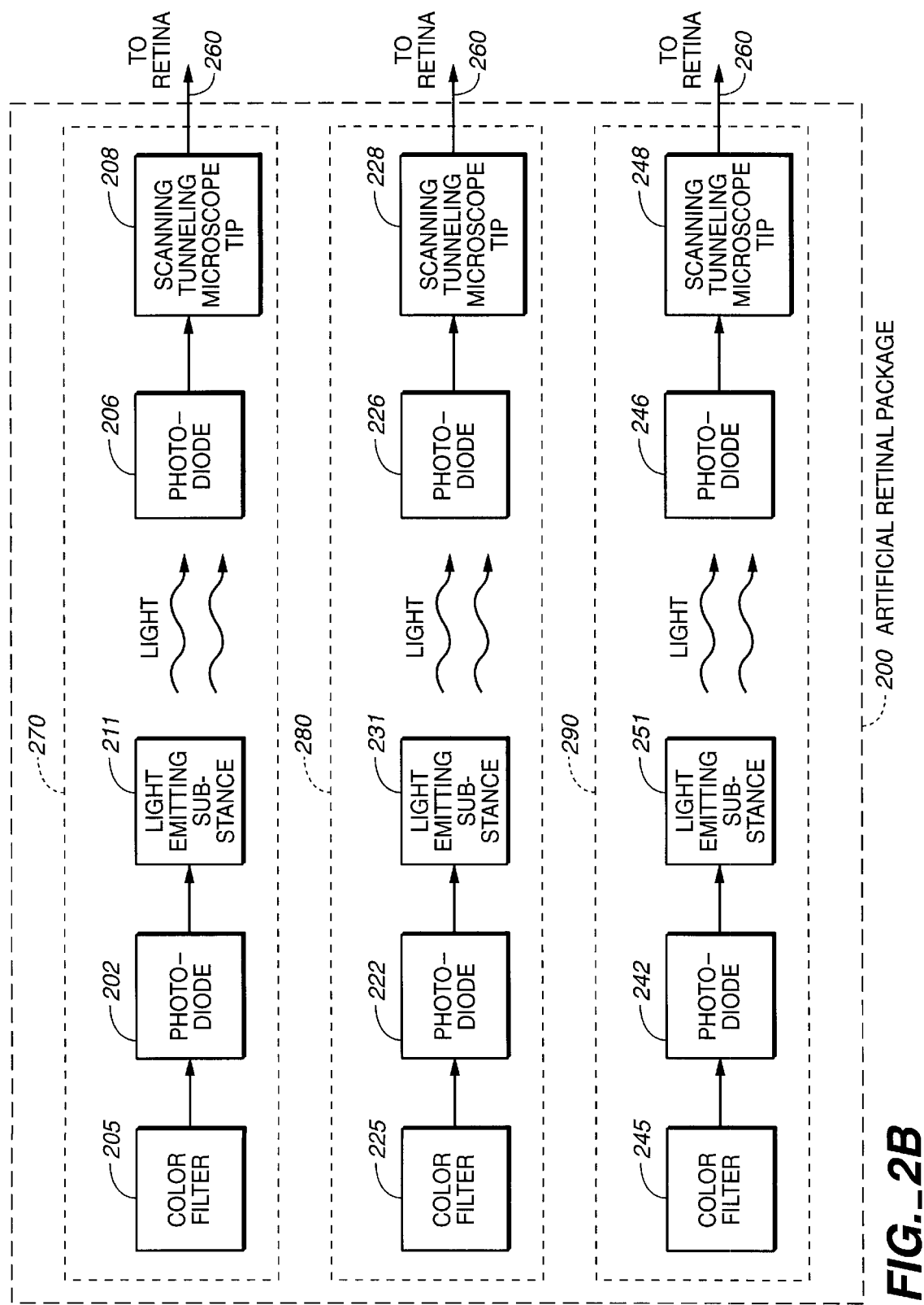
FIG._2B

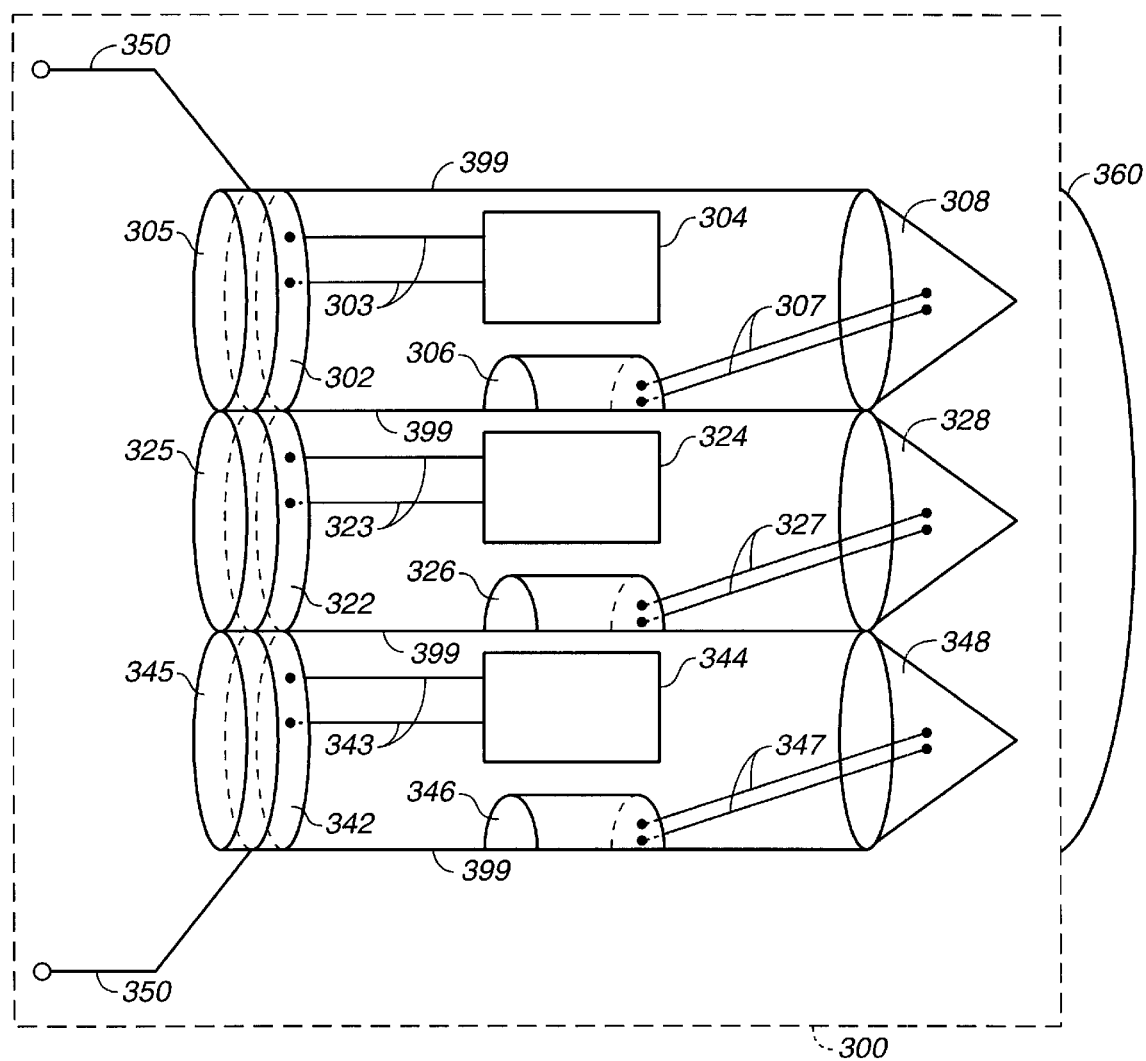
FIG._3A

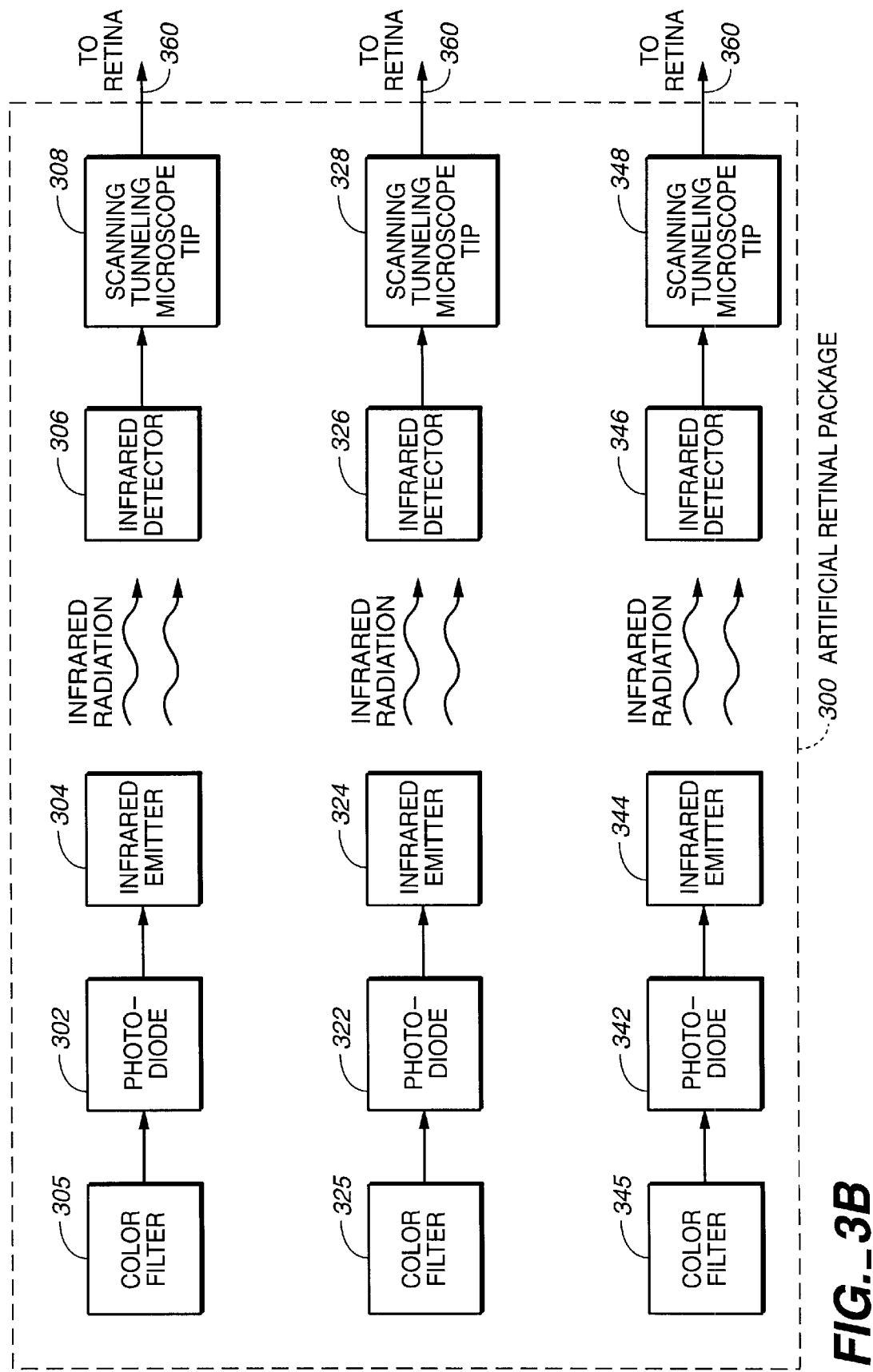
FIG._3B

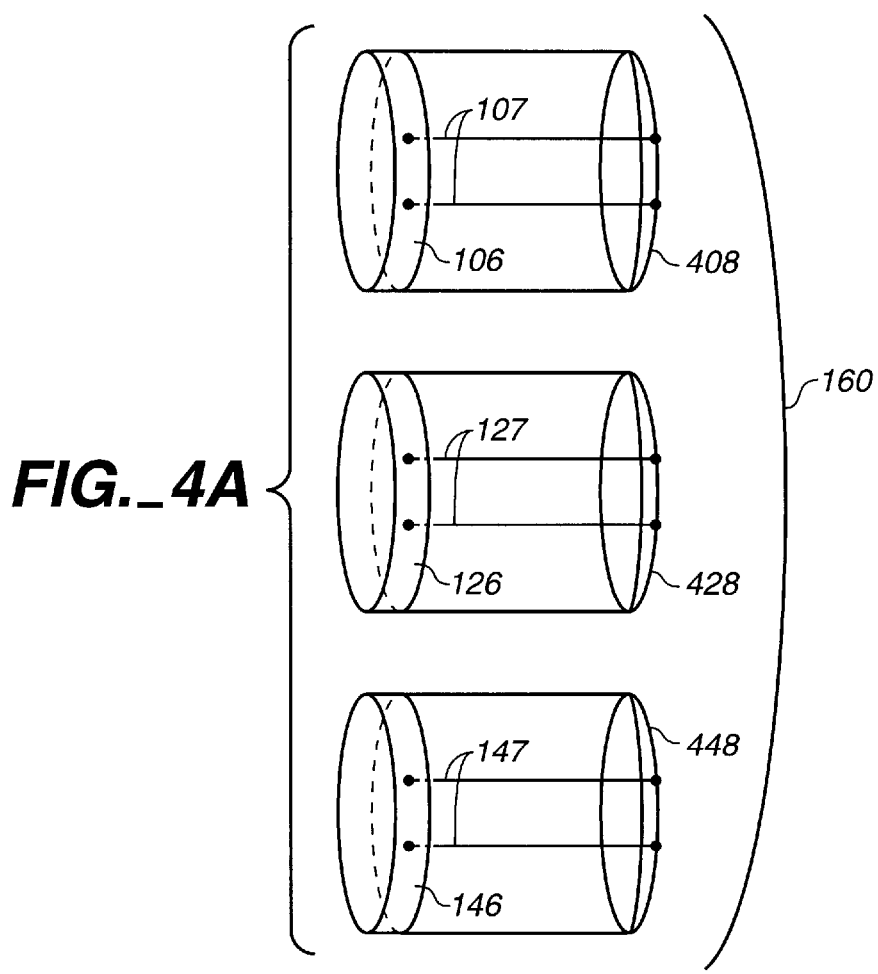
FIG._4A
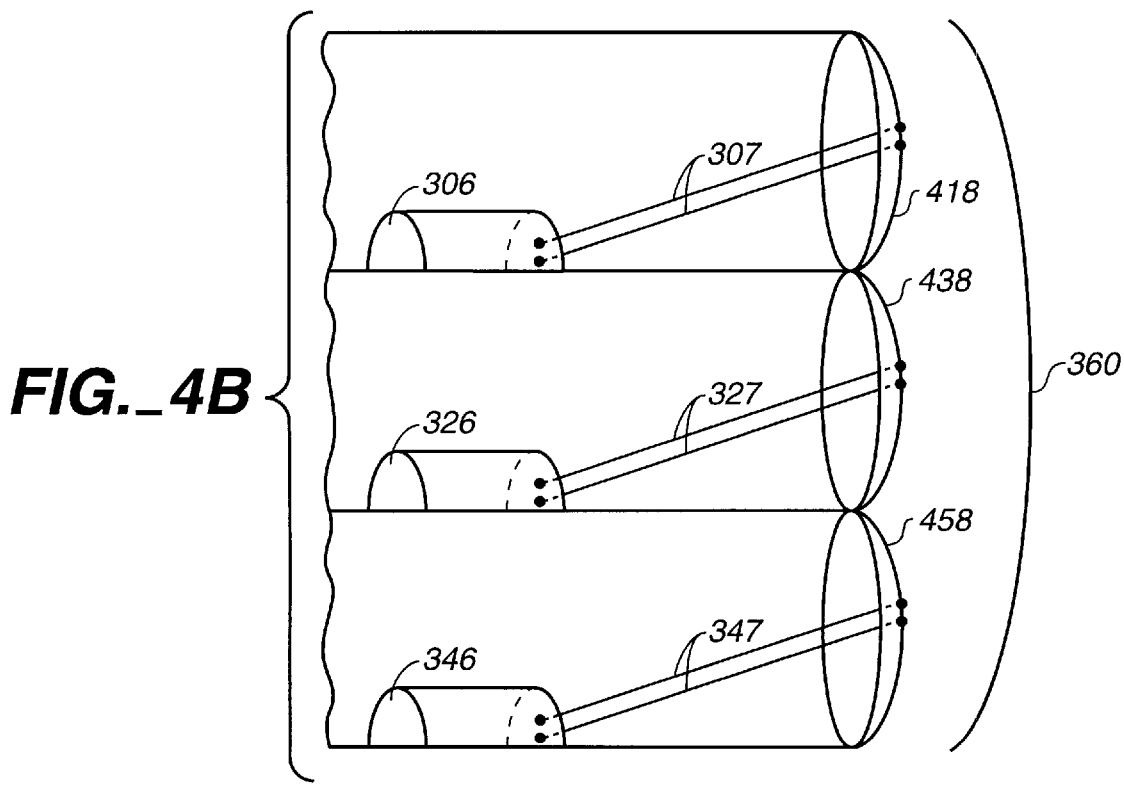
FIG._4B

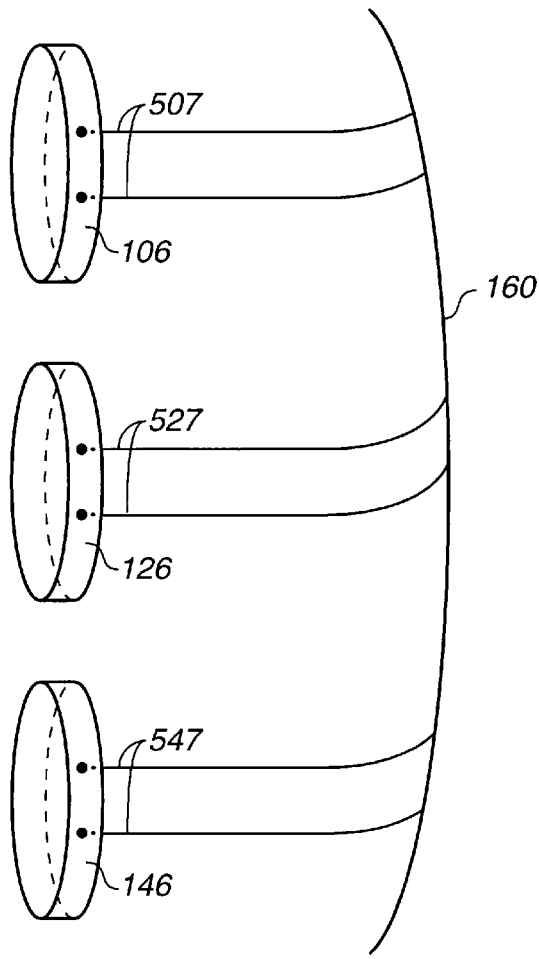
FIG._5A
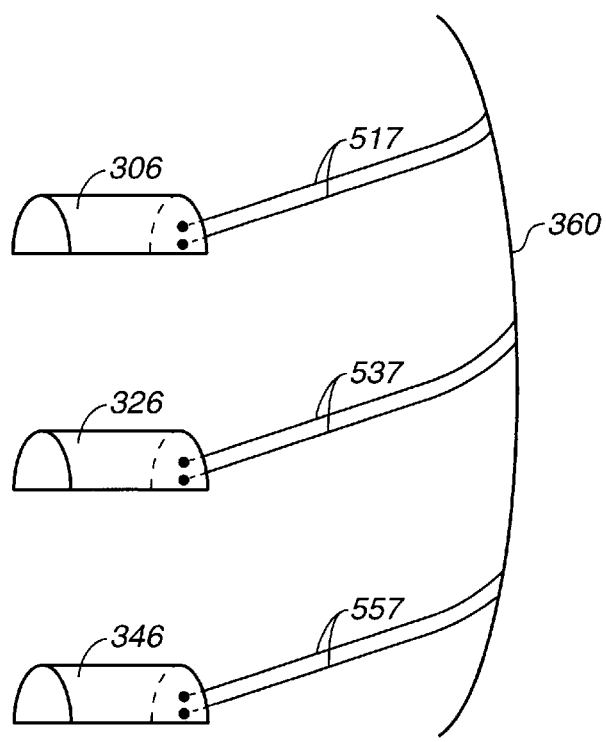
FIG._5B

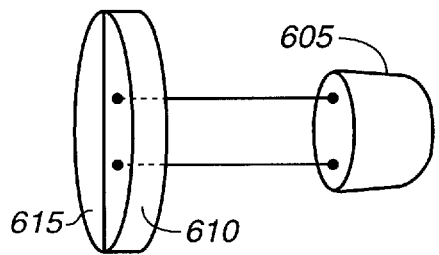
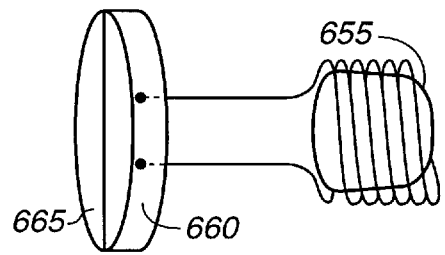
FIG._6A  FIG._6B
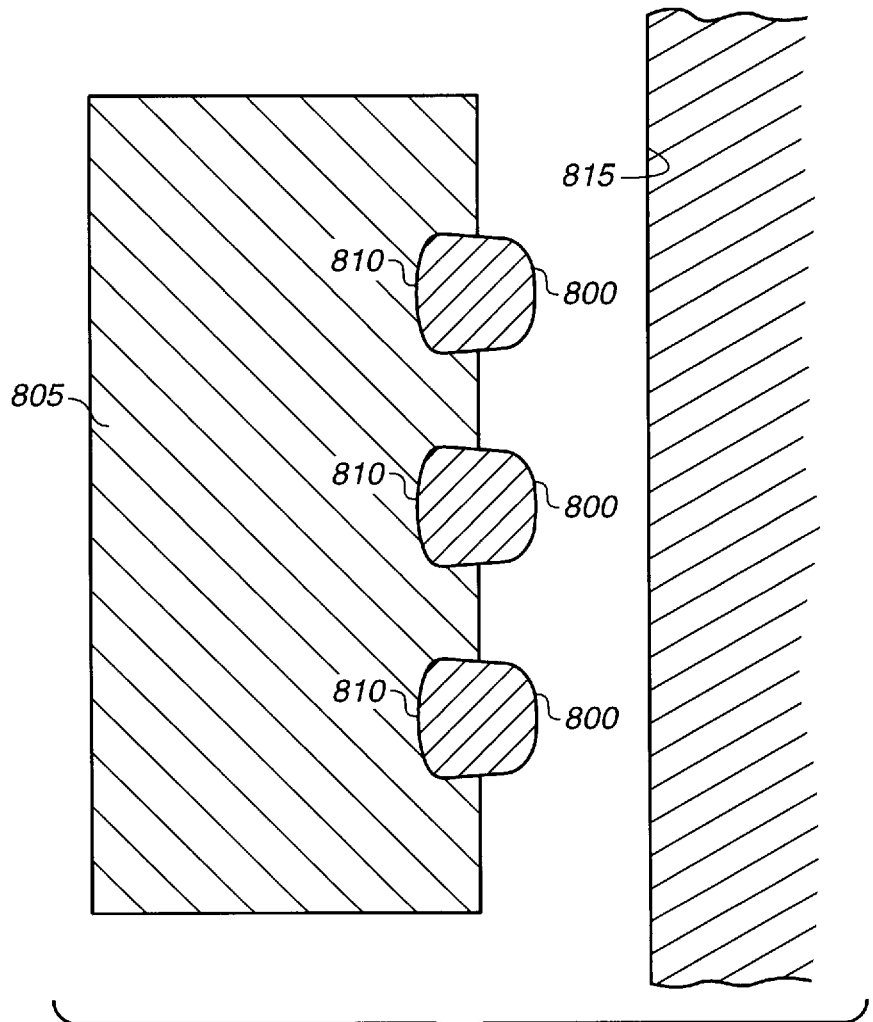
FIG._8

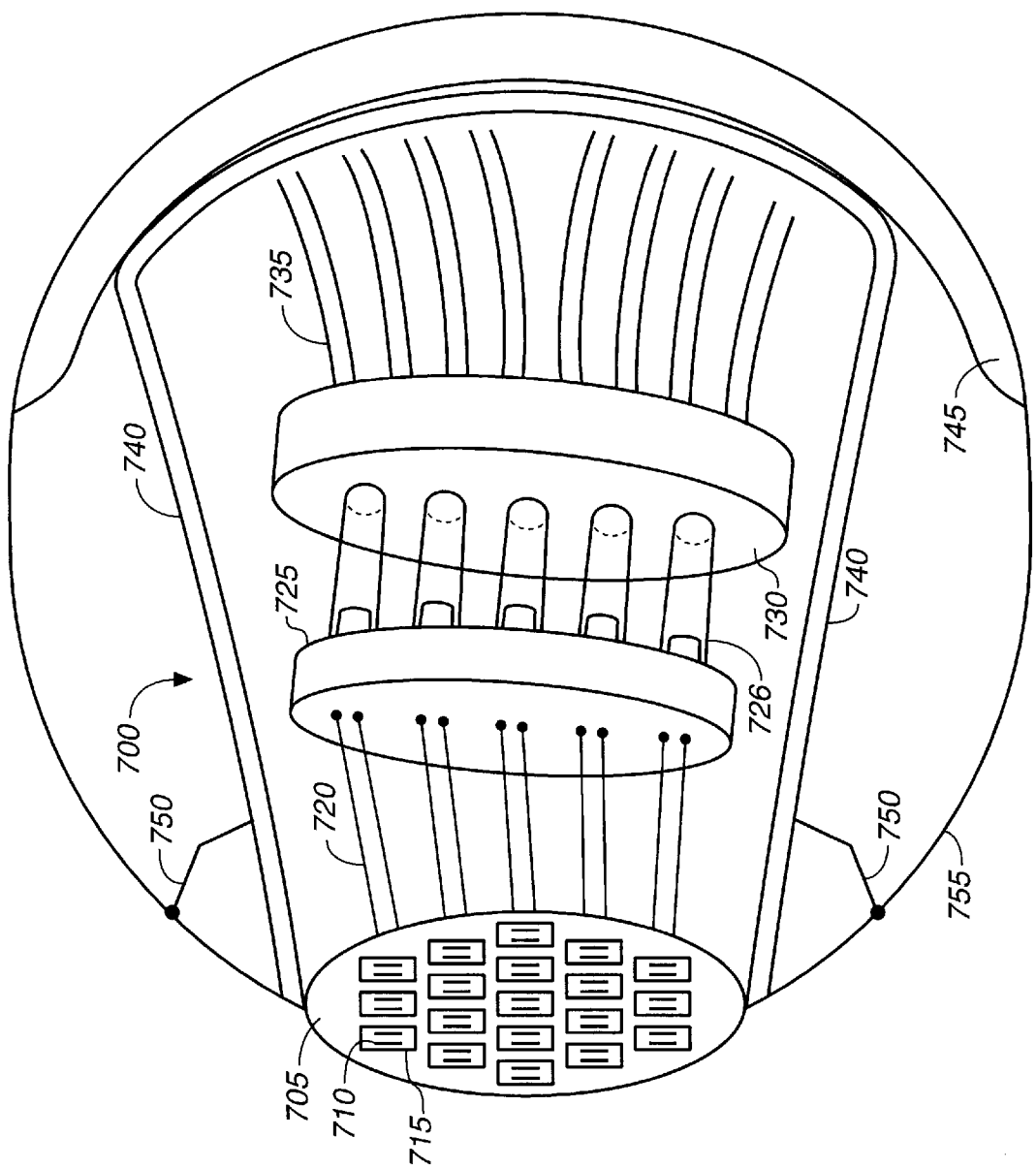
FIG._7

ARTIFICIAL RETINA

BACKGROUND OF THE INVENTION

The present invention relates to artificial human implantable devices. More specifically, the present invention relates to an artificial retinal implant device.

The human visual process is complex and has many aspects that are not yet well understood. However, it is well known that the retina is an essential element for human vision. The present understanding of the physiological process of vision in humans can be summarized as follows.

Light entering the eye is focused by the cornea and lens onto the retina. The retina comprises layers of rods and cones. Additionally, the retina comprises horizontal, bipolar and amacrine cells. Finally, the retina comprises a layer of ganglion (nerve) cells.

The light penetrates the relatively transparent outer layer of the retina and is intercepted by the rod and cone cells. In response to the incoming light, the rod and cone cells initiate a neuro-electrochemical reaction. The neuro-electrochemical reaction initiated by the rod and cone cells stimulates the ganglion cells via the bipolar, horizontal and amacrine cells or a subset thereof. The ganglion cells form the terminus of the optic nerve. The optical nerve transmits the neuro-electrochemical signal to the Lateral Geniculate Nucleus (LGN) which then transmits an amplified version of the signal to the brain's occipital lobe. Once the occipital lobe receives the proper stimulation, the brain "sees".

A damaged retina results in the loss of partial or total sight, as the retina is needed to convert the incoming visible light energy into the neuro-electrochemical signal needed by the brain. There are a number of retinal ailments, such as diabetic retinopathy, macular degeneration, retinitis pigmentosa, etc., which partially or completely destroy the retina's ability to intercept light and convert it into a corresponding neuro-electrochemical signal. Therefore, a person with one of the above ailments either partially or entirely loses his or her sight. Unfortunately, there are no known medications or surgical techniques for curing the above ailments and restoring the retina so that it can serve its proper role in the visual process.

As a result, researchers are actively seeking a way in which to create an artificial retina that would serve the function of a real human retina. The artificial retina recently suggested by these researchers is rather bulky as it includes a camera, mounted on eyeglasses, that captures visual images using a charge-coupled device (CCD) sensor. The CCD sensor digitizes the visual images intercepted by the camera. The digital representations of the images are then beamed via laser pulses onto a microchip implanted in the eye. The microchip includes an electrode array and a stimulation circuit. Using the electrode array, the microchip converts the laser pulses into a pattern of electric signals. In theory, these signals would then stimulate the nearest ganglion cells, which would then transmit the information to the brain via the optic nerve, enabling the wearer of the artificial retina to perceive an image.

It is to be noted that the above suggested artificial retina has not yet been developed for human use nor has it been tested on human subjects. The researchers in the area have not yet been able to develop an implantable portion of the artificial retina that can be left in the human eye for an extended period of time without damaging the eye. Moreover, the researchers have put off dealing with the issue of the electrical interface between the device and the brain until the implantable portion of the device is ready for implantation in humans since they believe that optimizing the electrical interface requires feedback from experimental subjects, i.e., human subjects. As there are still key aspects of the proposed artificial retina that have yet to be designed and tested, the suggested artificial retina is far from being reduced to a practical working model.

In addition to not having been reduced to a usable model, the above mentioned artificial retina suffers from several disadvantages. First, the device is too large to be entirely placed inside the eye. This is mostly a result of the use of a camera, which is placed on eyeglasses, to capture the visual images. The bulky nature of the device makes it both heavy and aesthetically unappealing. Second, since the device is not entirely implanted in the eye, it likely will suffer from reliability problems. Additionally, since the device is not entirely placed in the eye, the user of the implant must either continuously wear the eyeglasses with the camera disposed thereon or keep it near by for wearing when needed. When not wearing the eyeglass-camera combination, the user of the artificial retina must have a way of accessing the eyeglass-camera combination without the benefit of normal vision, as the user's vision is at least partially and perhaps totally impaired without the device. Moreover, the eyeglass-camera combination can be misplaced, which may subject the owner to the expense of purchasing a new eyeglass-camera combination. Finally, it may be difficult or impractical to expect the laser beam to reliably remain focused on the implant in the eye.

Therefore, it is desirable to have a retinal implant that is entirely insertable in the eye and overcomes the disadvantages associated with the implant described above.

SUMMARY OF THE INVENTION

The present invention encompasses providing an artificial retina that is sufficiently small so as to be fully implantable in the human eye.

Broadly stated, the artificial retina of the present invention comprises a light sensing element to sense incoming light and produce an output signal; an emitter element coupled to the light sensing element, where the emitter element senses the output of the light sensing element and emits an output in response thereto; a detector element which senses the output of the emitter element and produces an output signal whose magnitude is proportional to the intensity of the incoming light; and a coupler for coupling the output of the detector element to the retinal nerves.

In a preferred embodiment of the present invention, an artificial retina system comprises an array of artificial retinas, wherein each artificial retina comprises: a first photodiode, wherein said first photodiode produces an output signal in response to light impinging on said first photodiode; a color filter disposed in front of said first photodiode such that said first photodiode receives light having wavelengths within a wavelength band corresponding to a particular color; a light emitting diode (LED) or a microlaser system, wherein said LED is coupled to said first photodiode, further wherein said LED receives the output signal of said first photodiode and produces an output in response to the output of said first photodiode; a second photodiode, wherein said second photodiode senses the output of said LED and produces an output signal whose magnitude is proportional to the output of said LED; and a coupler, wherein said coupler couples the output of said second photodiode to the retina.

In a preferred embodiment of the present invention, each artificial retina in the array of artificial retinas is enclosed in a white opaque plastic material so as to optically and/or thermally isolate the artificial retinas from each other.

In a preferred embodiment of the present invention, the artificial retina array is housed in a plastic housing made of a material similar in composition to those used for artificial lenses such as those used in cataract lens replacements.

In one embodiment of the present invention, the first photodiodes of the artificial retina array are built into an artificial lens preferably in a square matrix. Each of the first photodiodes built into the artificial lens is covered by a color filter.

In one embodiment of the present invention, the coupler is a scanning tunneling microscope (STM) tip. The STM tip receives an electrical signal from the second photodiode and transmits an electrical signal to the retinal nerves. STM tips are well known in the art and are basically metal wires that are very finely sharpened at one end. The STM tip resembles a cone. In a preferred embodiment, the STM tip is made of platinum. The unsharpened end of the STM tip is coupled to the second photodiode while the sharpened end is directed towards the retina for releasing current at a specific point on the retina.

Another embodiment of the artificial retina of the present invention comprises a metal sheet instead of an STM tip. In this embodiment, the metal sheet is disposed between the second photodiode and the retinal nerve. The metal sheet receives the electrical signal output from the second photodiode and in response transmits an electrical signal to the retinal nerves. In a preferred embodiment, the metal sheet is made of copper and has a curvature corresponding to the curvature of the retina at the area near which the metal sheet is disposed.

In another embodiment, the second photodiode transmits its output to the retina by a very fine wire directly coupled to the retina. The wire is preferably made of platinum or copper. In a preferred embodiment, the very fine wire is encased in a plastic material such as those used to make artificial lenses.

In another embodiment of the artificial retina of the present invention, the first photodiode is coupled to a container containing a light emitting substance ("LES container"). The light emitting substance, like the LED, emits light in response to the output signal of the first photodiode. The light emitted by the light emitting substance is detected by a second photodiode, which outputs a signal to the retina via an STM tip, a metal sheet or a very fine wire.

In yet another embodiment, an infrared (IR) emitter is coupled to the first photodiode. The IR emitter emits IR radiation in response to the output signal of the first photodiode. The IR radiation is detected by an IR detector, which produces an output signal in response to this IR radiation. The output signal from the IR detector is a transmitted to the retina. In one embodiment, the output signals of the IR detector is transmitted to the retina via an STM tip. In another embodiment, the output signal is transmitted to the retina via a metal sheet. In yet another embodiment, the output signal is transmitted to the retina by a very fine wire coupled to the retina.

Accordingly, it is an object of the present invention to provide an artificial retina that is fully implantable in a human eye.

It is another object of the present invention to provide an artificial retina that restores some vision to those with retinal ailments such as retinitis pigmentosa, macular degeneration, diabetic retinopathy, etc. which at least partially impair sight.

It is another object of the present invention to provide an artificial retina system comprising an array of such artificial retinas.

These and other objects of the present invention will become apparent to those skilled in the art from the following detailed description of the invention, the accompanying drawings, and the appended claims.

BRIEF DESCRIPTION OF THE SEVERAL VIEWS OF THE DRAWING

FIG. 1A is a side perspective view of one embodiment of an artificial retina system of the present invention.

FIG. 1B is a schematic representation of the artificial retina system of the present invention shown in FIG. 1A.

FIG. 2A is a side perspective view of another embodiment of an artificial retina system of the present invention.

FIG. 2B is a schematic representation of the artificial retina system of the present invention shown in FIG. 2A.

FIG. 3A is a side perspective view of yet another embodiment of an artificial retina system of the present invention.

FIG. 3B is a schematic representation of the artificial retina system of the present invention shown in FIG. 3A.

FIG. 4A is a side perspective view of another embodiment of the interface between the second photodiodes and the retina.

FIG. 4B is a side perspective view of yet another embodiment of the interface between the second photodiodes and the retina.

FIG. 5A is a side perspective view of another embodiment of the interface between the infrared detector and the retina.

FIG. 5B is a side perspective view of yet another embodiment of the interface between the infrared detector and the retina.

FIG. 6A shows a side perspective view of two photodiodes coupled to a light emitting diode.

FIG. 6B shows a side perspective view of two photodiodes coupled to a light emitting substance container.

FIG. 7 shows a side perspective view of another embodiment of an artificial retina system of the present invention implanted in an eye.

FIG. 8 shows a cross sectional view of wires encased in a plastic material.

DETAILED DESCRIPTION OF THE INVENTION

FIG. 1A shows one embodiment of an artificial retina system of the present invention. Artificial retina system 100 is sufficiently small so as to be fully implantable in a human eye, more specifically in the vitreous body of an eye. Artificial retina system 100 comprises anchoring probes 150 which anchor artificial retina system 100 in the eye. The anchoring probes 150 are preferably implanted in the ciliary muscle of the eye. Artificial retina system 100 also comprises an array of artificial retinas, such as artificial retinas 170, 180 and 190. Each of the artificial retinas comprises a first photodiode, a light emitting diode (LED), a second photodiode and a scanning tunneling microscope (STM) tip. In one embodiment of the present invention, the first photodiodes used in the artificial retinas are Type # G1118 manufactured by Hamamatsu Corporation of New Jersey. STM tips are well known in the art and are made of metal wires that are very finely sharpened at one end. The STM tips resemble cones. In the drawings, the size of the cones has been exaggerated for illustrative purposes. In a preferred embodiment, the STM tip is made of platinum. Artificial retina 170 comprises first photodiode 102, LED 104, second photodiode 106 and STM tip 108. Similarly artificial retina 180 comprises first photodiode 122, LED 124, second photodiode 126 and STM tip 128 while artificial retina 190 comprises first photodiode 142, LED 144, second photodiode 146 and STM tip 148. Artificial retinas 170, 180 and 190 also preferably comprise color filters 105, 125 and 145, respectively, which are disposed in front of first photodiodes 102, 122 and 142, respectively. First photodiodes 102, 122 and 142 are respectively coupled to LEDs 104, 124 and 144 by connectors 103, 123 and 143. Second photodiodes 106, 126 and 146 intercept light emitted by LEDs 104, 124 and 144, respectively. Second photodiodes 106, 126 and 146 are, in turn, respectively coupled to STM tips 108, 128 and 148 via connectors 107, 127 and 147.

In a preferred embodiment, artificial retinas 170, 180 and 190 are optically isolated such that light transmitted by the LED of one artificial retina does not impinge on the second photodiode of another artificial retina. In one embodiment, artificial retinas 170, 180 and 190 are each substantially encased in a white opaque plastic material 199 to optically isolate each artificial retina from the other artificial retinas in the artificial retina system 100. In a preferred embodiment, the artificial retinas 170, 180 and 190 are substantially encased by the white opaque plastic material 199 such that the color filters, the photodiodes and the STM tips are not encased by the white opaque plastic material.

The operation of artificial retina system 100 will now be explained in relation to FIG. 1B which shows a schematic diagram of artificial retina system 100.

Incoming light is first filtered by color filters 105, 125 and 145. Each of the color filters only transmits light having wavelengths that fall within a wavelength band corresponding to a particular color and reflect light having wavelengths outside the wavelength band. In other words, each color filter passes only light of a particular color. Thus, for example, color filters 105, 125 and 145 would only transmit light corresponding to the colors red, green and blue, respectively. Photodiodes 102, 122 and 142 would then only receive light corresponding to the colors red, green and blue, respectively. In a preferred embodiment, photodiodes 102, 122 and 142 would each be particularly sensitive to light having energies corresponding to a particular color. For example, photodiodes 102, 122 and 142 would be particularly sensitive to light energies corresponding to the colors red, green and blue, respectively. In other words, photodiodes 102, 122 and 142 have visible light sensitivities that peak in red, green and blue, respectively.

In response to the light they sense, photodiodes 102, 122 and 142 send an electrical signal to LEDs 104, 124 and 144, respectively, by connectors 103, 123 and 143, respectively. The magnitude of the electrical signal each of the photodiodes 102, 122 and 142 sends is proportional to the intensity of light that each intercepts. In response to the electrical signals from the first photodiodes 102, 122 and 142, each of the LEDs 104, 124 and 144 emits light whose intensity is proportional to the magnitude of the electrical signal it receives from photodiodes 102, 122 and 142, respectively. The light emitted by LEDs 104, 124 and 144 is intercepted by the second photodiodes 106, 126 and 146, respectively. In a preferred embodiment, the second photodiodes 106, 126 and 146 are sensitive to visible light. Moreover, in a preferred embodiment, the second photodiode whose corresponding color filter transmits red light has an extended red sensitivity. In response to the light they intercept, photodiodes 106, 126 and 146 transmit an electrical signal to the STM tips 108, 128 and 148, respectively, via connectors 107, 127 and 147, respectively. The electrical signal transmitted by the second photodiodes 106, 126 and 146 is proportional to the intensity of light intercepted by each. The STM tips 108, 128 and 148 then transmit the electrical signals received from photodiodes 106, 126 and 146 to the retina 160. Each STM tip transmits the electrical signal to the retina 160 through the pointed end of its cone, which is pointed at the retina 160. Therefore, the STM tips 108, 128 and 148 allow concentrating electrical signals at specific points on the retina 160. In a preferred embodiment, the sharpened tip of each STM tip is set at a distance of approximately 0.5 nm from the retina 160. In another embodiment, the STM tip may simply be in contact with the surface of retina 160.

Since, in each stage, the magnitude of the signal transmitted by an element is proportional to the magnitude of the signal received by that same element, the electrical signal transmitted by the second photodiodes 106, 126 and 146 will be directly proportional to the intensity of light intercepted by the first photodiodes 102, 122 and 142, respectively. Similarly, the magnitude of the electrical current transmitted to the retina by an STM tip will be proportional to the intensity of incoming light having energies corresponding to those intercepted by that STM tip's corresponding first photodiode.

It is to be appreciated by those skilled in the art that two layers of photodiodes, i.e., a first photodiode and a second photodiode, are preferably used in each artificial retina so as to sufficiently attenuate the current transmitted by the artificial retina. A current that is significantly greater than currents naturally produced in the human eye may severely damage or perhaps burn tissue in the eye. Therefore, it is preferable that the artificial retina output a current within the range of currents normally transmitted by a human retina. In another embodiment, it may be possible to use only one photodiode (or light sensing element) layer, wherein the photodiode (or light sensing element) outputs a current within the range of currents normally transmitted by the retina.

The electrical signals transmitted to the retina will be in the range of a few picoamps, which is the range of currents naturally produced in a human eye. The electrical signals transmitted to the retina are intercepted by the ganglion cells, which then transmit a corresponding signal along the optic nerve to the Lateral Geniculate Nucleus (LGN). The LGN then sends a corresponding signal to the occipital lobe. The signals received at the occipital lobe allow the brain to "see".

FIGS. 2A and 2B respectively show a side perspective view and a schematic diagram of another embodiment of an artificial retina system of the present invention. Artificial retina system 200, shown in FIG. 2A, comprises an array of artificial retinas, i.e., artificial retinas 270, 280 and 290, is fully implantable in a human eye, more specifically in the vitreous body of an eye, and basically operates in substantially the same way as artificial retina system 100, shown in FIG. 1A. Color filters 205, 225 and 245, like the color filters of artificial retina 100, filter the incoming light and allow the transmission of light corresponding to a particular color. The transmitted light from color filters 205, 225 and 245 is detected by first photodiodes 202, 222 and 242, respectively. Artificial retina system 200 is different from artificial retina system 100 in that artificial retina system 200 uses containers containing a light emitting substance ("LES containers") rather than LEDs. LES containers 204, 224 and 244 are preferably made of an impermeable, transparent material that has a high melting point and good thermal conductivity. LES containers 204, 224 and 244 are filled with light emitting substances 211, 231 and 251, respectively. The light emitting substances 211, 231 and 251 may be the same substance such as NaCl crystals which have been x-ray irradiated. Alternatively, each LES container may contain a different light emitting substance. The LES containers 204, 224 and 244 are coupled to photodiodes 202, 222 and 242, respectively, via connectors 203, 223 and 243, respectively. The containers 204, 224 and 244 are wrapped by connectors 203, 223 and 243, respectively. Connectors 203, 223 and 243 can, for example, be made of electrically conducting wires having a sufficiently high resistivity so as to heat up the LES containers when an electrical current is passed through them. The heat from the connectors 203, 223 and 243 warms the light emitting substances, 211, 231 and 251, respectively, in the containers to a sufficiently high temperature so as to cause them to emit light. Light emitted by the light emitting substances 211, 231 and 251 is detected by the second photodiodes 206, 226 and 246, respectively. The second photodiodes 206, 226 and 246 are sensitive to visible light. Moreover, in a preferred embodiment, the second photodiode, whose corresponding color filter transmits red light, has an extended red sensitivity. In response to the light they detect, photodiodes 206, 226 and 246 transmit an electrical signal to the STM tips 208, 228 and 248, respectively, via connectors 207, 227 and 247, respectively. The STM tips 208, 228 and 248 then transmits the electrical signal received from photodiodes 206, 226 and 246 to the retina 260.

In a preferred embodiment, artificial retinas 270, 280 and 290 are optically isolated such that light emitted by the LES container of one artificial retina does not impinge on the second photodiode of another artificial retina. In a preferred embodiment, artificial retinas 270, 280 and 290 are also thermally isolated such that heat from the connector or LES container of one artificial retina is not transferred to the connector or LES of another artificial retina. In one embodiment, artificial retinas 270, 280 and 290 are each substantially encased in a white opaque plastic material 299 to optically and thermally isolate each artificial retina from the other artificial retinas in the artificial retina system 200. In a preferred embodiment, the artificial retinas 270, 280 and 290 are substantially encased by the white opaque plastic material 299 such that the color filters, the photodiodes and the STM tips are not encased by the white opaque plastic material.

As in artificial retina system 100, the signal transmitted by each element in artificial retina system 200 is proportional to the signal detected by that element. Consequently, the electrical signal transmitted by the second photodiodes 206, 226 and 246 will be directly proportional to the intensity of light detected by the first photodiodes 202, 222 and 242, respectively. Similarly, the magnitude of the electrical current transmitted to the retina by an STM tip will be proportional to the intensity of incoming light having energies corresponding to those intercepted by the first photodiode which is part of the same artificial retina as the STM tip.

FIGS. 3A and 3B respectively show a side perspective view and a schematic diagram of yet another embodiment of the present invention. Artificial retina system 300 shown in FIG. 3A is sufficiently small so as to be fully implantable in a human eye, more specifically in the vitreous body of an eye. Artificial retina system 300 comprises anchoring probes 350 which anchor artificial retina system 300 in the eye. The anchoring probes 350 are preferably implanted in the ciliary muscle of the eye. Artificial retina system 300 also comprises an array of artificial retinas such as artificial retinas 370, 380 and 390. Each of the artificial retinas comprises a photodiode, an infrared (IR) emitter, an IR detector and a STM tip. In one embodiment of the present invention, the IR emitters may be of the type sold by Radio Shack under Radio Shack's Catalog Number 276–142. Artificial retina 370 comprises photodiode 302, IR emitter 304, IR detector 306 and STM tip 308. Similarly artificial retina 380 comprises photodiode 322, IR emitter 324, IR detector 326 and STM tip 328 while artificial retina 390 comprises photodiode 342, IR emitter 344, IR detector 346 and STM tip 348. Artificial retinas 370, 380 and 390 also preferably comprise color filters 305, 325 and 345, respectively, which are disposed in front of photodiodes 302, 322 and 342, respectively. Photodiodes 302, 322 and 342 are respectively coupled to IR emitters 304, 324 and 344 by connectors 303, 323 and 343. IR detectors 306, 326 and 346 intercept IR radiation emitted by IR emitters 304, 324 and 344, respectively. IR detectors 306, 326 and 346 are, in turn, respectively coupled to STM tips 308, 328 and 348 via connectors 307, 327 and 347.

In a preferred embodiment, artificial retinas 370, 380, and 390 are thermally and optically isolated such that IR radiation emitted by the IR emitter of one artificial retina does not impinge on the IR detector of another artificial retina. In one embodiment, artificial retinas 370, 380 and 390 are each substantially encased in a white opaque plastic material 399 to thermally and optically isolate each artificial retina from the other artificial retinas in the artificial retina system 300. In a preferred embodiment, the artificial retinas 370, 380 and 390 are substantially encased by the white opaque plastic material 399 such that the color filters, the photodiodes and the STM tips are not encased by the white opaque plastic material.

Incoming light is first filtered by color filters 305, 325 and 345. Each of the color filters only transmits light corresponding to a particular color and reflect light that does not correspond to that particular color. Thus, for example, color filters 305, 325 and 345 would only transmit light corresponding to the colors red, green and blue, respectively. Photodiodes 302, 322 and 342 would then only receive light having energies corresponding to the colors red, green and blue, respectively. In a preferred embodiment, photodiodes 302, 322 and 342 would each be particularly sensitive to light corresponding to a particular color. For example, photodiodes 302, 322 and 342 would be particularly sensitive to red, green and blue light, respectively.

In response to the light they detect, photodiodes 302, 322 and 342 send an electrical signal to IR emitters 304, 324 and 344, respectively, by connectors 303, 323 and 343, respectively. The magnitude of the electrical signal each of the photodiodes 302, 322 and 342 sends is proportional to the intensity of light that each detects. In response to the electrical signals from the first photodiodes 302, 322 and 342, each of the IR emitters 304, 324 and 344 emits IR radiation whose intensity is proportional to the magnitude of the electrical signal it receives from photodiodes 302, 322 and 342, respectively. The IR radiation emitted by IR emitters 304, 324 and 344 is detected by the IR detectors 306, 326 and 346, respectively. In response to the IR radiation they detect, IR detectors 306, 326 and 346 transmit an electrical signal to the STM tips 308, 328 and 348, respectively, via connectors 307, 327 and 347, respectively. The electrical signal transmitted by the IR detectors 306, 326 and 346 is proportional to the intensity of IR radiation detected by each. The STM tips 308, 328 and 348 then transmit the electrical signals received from the IR detectors 306, 326 and 346 to the retina 360. Each STM tip transmits the electrical signal to the retina 360 through the its pointed tip which allows concentrating the electrical signals at specific points on the retina 360.

Since, in each stage, the magnitude of the signal transmitted by an element is proportional to the magnitude of the signal detected by that same element, the electrical signal transmitted by the IR detectors 306, 326 and 346 will be directly proportional to the intensity of light detected by the first photodiodes 302, 322 and 342, respectively. Similarly, the magnitude of the electrical current transmitted to the retina by an STM tip will be proportional to the intensity of incoming light detected by the first photodiode which is part of the same artificial retina as the STM tip.

FIG. 4A shows an alternative embodiment of the coupling between the second photodiodes 106, 126 and 196 and the retina 160 in artificial retina system 100 of FIG. 1. In FIG. 4A, the second photodiodes 106, 126 and 146 are coupled to metal sheets 408, 428 and 448 instead of STM tips. The metal sheets 408, 428 and 448 are made of a metal, such as copper, and are placed near the surface of the retina 160. The metal sheets 408, 428 and 448 are preferably arched so as to conform to the curvature of the retina 160 at the area near which they are placed. The electrical signal transmitted by the photodiodes 106, 126 and 146 is received by the metal sheets 408, 428 and 448 and then transmitted to the retina 160. The metal sheets 408, 428 and 448, unlike the STM tips, do not concentrate the electrical signal sent to the retina at a specific point on the retina. Instead, the current is dispersed on the surface of the metal sheet and is consequently received over a corresponding surface on the retina. In a preferred embodiment, the metal sheets 408, 428 and 448 are placed at a distance of approximately 0.5 nm from the retina 160. In another embodiment, the metal sheets 408, 428 and 448 contact the surface of the retina 160.

Similarly, artificial retina systems 200 and 300 may be modified such that their STM tips are replaced by metal sheets such as those shown in FIG. 4A, which allow dispersing the electrical signal to the retina on its surface rather than concentrating it on a specific point on the retina. For example, FIG. 4B shows IR detectors 306, 326 and 346 coupled to metal sheets 418, 438 and 458, respectively.

In yet another embodiment of the interface between the second photodiodes and the retina, very fine metal wires are coupled to the second photodiodes and the retina. FIG. 5A shows second photodiodes 106, 126 and 146 coupled to the retina by the metal wires 507, 527 and 547, respectively. Metal wires are preferably made of platinum and have a diameter of approximately 0.5–10 $\mu$m. In another embodiment, the metal wires are made of copper. The metal wires are coupled to the second photodiodes at one end and to the retina at the other. The contact between the metal wires 507, 527 and 547 and retina 360 will increase the probability that the current in the wires will stimulate a large number of ganglion cells in the retina.

Similarly, artificial retina systems 200 and 300 may be modified such that their STM tips are replaced by very fine metal wires such as those used in FIG. 5A. FIG. 5B shows IR detectors 306, 326 and 346 coupled to metal wires 517, 537 and 557, respectively. The metal wires 517, 527 and 557 are in turn coupled to the retina 360 by directly contacting the retina.

In yet another embodiment of the present invention, each of the LES containers or LEDs is coupled to a plurality of photodiodes which are coupled in series. For example, as shown in FIG. 6A, LED 605 is coupled to two photodiodes which are coupled in series such that the amount of energy transmitted to LED 605 is twice as large as it would be if LED 605 were coupled to a single photodiode. Similarly, FIG. 6B shows LES container 655 coupled to photodiodes 660 and 665 which are coupled in series.

FIG. 7 shows another embodiment of the artificial retina system of the present invention implanted in an eye. Artificial retina system 700 is shown as being implanted in eye 755. Artificial retina system 700 comprises artificial lens 705, photodiodes 710, color filters 715, connectors 720, emitters 725, detectors 730, couplers 735 and anchoring probes 750. Artificial lens 705 is preferably made of the same material as that used for making artificial lenses, such as those used for cataract lens replacement. Photodiodes 710 are built into the artificial lens 705 and are covered by color filters 715 such that a color filter is disposed in front of each photodiode. The maximum number of photodiodes that would fit into the artificial lens 705 are built into artificial lens 705. In a preferred embodiment, the photodiodes 710 are built into artificial lens 705 in a square matrix. Photodiodes 710 are coupled to emitters 725 by connectors 720. Signals emitted by emitters 725 are detected by detectors 730. In a preferred embodiment, white opaque plastic material casings 726, which are preferably cylindrical, are disposed between emitters 725 and detectors 730, such that each detector receives a signal from only its corresponding emitter. This insures that each emitter-detector set is optically and thermally isolated from the other emitter-detector sets in the artificial retina system 700. Emitters 725 may be LEDs (for example, an LED sheet), IR emitters, or microlaser devices (for example, a microlaser sheet). Detectors 730 may be photodiodes or IR detectors. The detectors 730 emit signals which are transmitted to the retina 745 via wires 735, which rest-up against the retina 745. In a preferred embodiment, wires 735 are partially encased in a plastic material such as those used to make artificial lenses. The side of wires 735 adjacent the retina will not be encased in the plastic material so as to allow electrical contact between wires 735 and retina 745.

FIG. 8 shows a cross sectional view of metal wires 800 encased in plastic material 805. As can be seen in FIG. 8, wires 800 are placed in grooves 810 within plastic material 805 such that the side of wires 800 adjacent retina 815 is not enclosed by plastic material 805.

In another embodiment, wires 735 may be replaced by STM tips or metal sheets such as those shown in FIGS. 1A and 4A, respectively. It is to be noted that the STM tips and the metal sheets will not be enclosed in the plastic material which in the preferred embodiment will partially encase wires 735.

In a preferred embodiment, artificial retina system 700 also comprises housing material 740 which houses the components within the artificial retina system 700. Therefore, the array of artificial retinas in the artificial retina system 700 are encased in the housing material 740. The housing material 740 creates a barrier between the interior of the eye and the interior of the artificial retina system. This barrier prevents leakage of possibly toxic material from the artificial retina system to the eye and leakage of vitreous humor from the eye to the artificial retina system. Housing material 740 is preferably made of the same material as that used for making artificial lenses, such as those used for cataract lens replacement. It is to be noted that the housing material 740 substantially encases the artificial retina system. Housing material 740 does not entirely encase the artificial retina system since it preferably does not cover the artificial lens 705 or the sides of the metal wires 735 that are adjacent the retina 745.

While the present invention has been particularly described with respect to the illustrated embodiments, it will be appreciated that various alterations, modifications and adaptations may be made based on the present disclosure, and are intended to be within the scope of the present invention. While the invention has been described in connection with what is presently considered to be the most practical and preferred embodiments, it is to be understood that the present invention is not limited to the disclosed embodiments but, on the contrary, is intended to cover various modifications and equivalent arrangements included within the scope of the appended claims.

I claim:

1. An artificial retina for implantation in a human eye having a retina, said artificial retina comprising:
    a light sensing element to sense incoming visible light having an intensity, said light sensing element producing an output signal;
    an emitter element coupled to said light sensing element, wherein said emitter element senses said output signal of said light sensing element and emits an output;
    a detector element, wherein said detector element senses the output of said emitter element and produces an output signal whose magnitude is proportional to the intensity of said incoming visible light; and
    a coupler to couple the output signal of said detector element to the retina.

2. The artificial retina of claim 1, wherein said coupler is a scanning tunneling microscope (STM) tip.

3. The artificial retina of claim 2, wherein said STM tip comprises a cone having a tip, adapted to be disposed adjacent the retina.

4. The artificial retina of claim 1, wherein said coupler is a metal sheet disposed adjacent the retina.

5. The artificial retina of claim 4, wherein said metal is copper.

6. The artificial retina of claim 1, wherein said coupler is a wire.

7. The artificial retina of claim 1, wherein said emitter element is a light emitting element diode (LED).

8. The artificial retina of claim 7, wherein said detector element is a photodiode.

9. The artificial retina of claim 1, wherein said emitter element is an infrared (IR) emitter.

10. The artificial retina of claim 9, wherein said detector element is an IR detector.

11. The artificial retina of claim 1, wherein said emitter element is a container containing a light emitting substance.

12. The artificial retina of claim 11, wherein said detector element is a photodiode.

13. The artificial retina of claim 1, wherein said emitter element is a microlaser device.

14. The artificial retina of claim 13, wherein said detector element is an IR detector.

15. An artificial retina system for implantation into a human eye having a retina, said artificial retina system comprising:
    an array of artificial retinas connected together, wherein each artificial retina comprises:
        a light sensing element, wherein said light sensing element produces an output signal in response to light impinging on said light sensing element;
        an emitter element, wherein said emitter element is coupled to said light sensing element, further wherein said emitter element receives the output signal of said light sensing element and produces an output in response to the output of said light sensing element;
        a detector element, wherein said detector element senses the output of said emitter element and produces an output signal whose magnitude is proportional to the output of said emitter element; and
        a coupler, wherein said coupler couples the output of said detector element to the retina.

16. The artificial retina system of claim 15, wherein each said artificial retina further comprises a color filter disposed in front of said light sensing element such that each said light sensing element receives light having wavelengths in a wavelength band corresponding to one color.

17. The artificial retina system of claim 16, wherein each said light sensing element is sensitive to light having wavelengths in a wavelength band corresponding to a particular color.

18. The artificial retina system of claim 16, wherein said coupler comprises a scanning tunneling microscope (STM) tip.

19. The artificial retina system of claim 18, wherein said STM tip comprises a cone having a tip adapted to be disposed adjacent the retina.

20. The artificial retina system of claim 16, wherein said coupler comprises a metal sheet.

21. The artificial retina system of claim 20, wherein said metal is copper.

22. The artificial retina system of claim 16, wherein said coupler comprises a wire.

23. The artificial retina system of claim 15, wherein said emitter element is a light emitting diode (LED).

24. The artificial retina system of claim 23, wherein said detector element is a photodiode.

25. The artificial retina system of claim 15, wherein said emitter element is an infrared (IR) emitter.

26. The artificial retina system of claim 25, wherein said detector element is a an IR detector.

27. The artificial retina system of claim 15, wherein said emitter element is a container containing a light emitting substance.

28. The artificial retina system of claim 27, wherein said detector element is a photodiode.

29. The artificial retina system of claim 15, wherein said emitter element is a microlaser device.

30. The artificial retina system of claim 29, wherein said detector element is an IR detector.

31. The artificial retina system of claim 15 further comprising a plastic housing substantially encasing said array of artificial retinas.

32. The artificial retina system of claim 15, wherein each artificial retina is substantially encased by a white opaque plastic material.

* * * * *